(12) United States Patent
Akiba

(10) Patent No.: US 8,967,802 B2
(45) Date of Patent: Mar. 3, 2015

(54) OPHTHALMIC APPARATUS

(71) Applicant: Canon Kabushiki Kaisha, Tokyo (JP)

(72) Inventor: Shintaro Akiba, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/867,312

(22) Filed: Apr. 22, 2013

(65) Prior Publication Data

US 2013/0293837 A1    Nov. 7, 2013

(30) Foreign Application Priority Data

May 1, 2012    (JP) .................................. 2012-104885

(51) Int. Cl.
  *A61B 3/10*    (2006.01)
  *A61B 3/14*    (2006.01)
  *A61B 3/00*    (2006.01)

(52) U.S. Cl.
  USPC ............ 351/205; 351/208; 351/209; 351/245

(58) Field of Classification Search
  USPC ................................................. 351/200–246
  See application file for complete search history.

(56) References Cited

U.S. PATENT DOCUMENTS

| | | | |
|---|---|---|---|
| 7,237,897 B2 * | 7/2007 | Terabe | 351/222 |
| 7,762,666 B2 * | 7/2010 | Chang et al. | 351/210 |
| 8,670,126 B2 | 3/2014 | Kabetani et al. | |
| 2005/0012896 A1 * | 1/2005 | Fukuma et al. | 351/201 |
| 2009/0021696 A1 | 1/2009 | Chang et al. | |
| 2011/0181889 A1 | 7/2011 | Kabetani et al. | |
| 2012/0218519 A1 | 8/2012 | Akiba | |

FOREIGN PATENT DOCUMENTS

| | | |
|---|---|---|
| CN | 102192896 A | 9/2011 |
| CN | 202010143 U | 10/2011 |
| EP | 1 779 771 A1 | 5/2007 |
| JP | 2007-289663 A | 11/2007 |
| JP | 2010-148589 A | 7/2010 |
| WO | 2011/099236 A1 | 8/2011 |

OTHER PUBLICATIONS

Sep. 30, 2014 Chinese Official Action in Chinese Patent Appln. No. 201310157907.4.

* cited by examiner

*Primary Examiner* — Mohammed Hasan
(74) *Attorney, Agent, or Firm* — Fitzpatrick, Cella, Harper & Scinto

(57) ABSTRACT

An ophthalmic apparatus which is configured to inspect a plurality of eye characteristics of an eye to be examined which is fixed by a face support unit, the apparatus comprises: an optometric unit configured to include a first optometric portion including a first optical system for inspecting a first eye characteristic of the eye, and a second optometric portion including a second optical system for inspecting a second eye characteristic different from the first eye characteristic; and a changing unit configured to change a direction of the optometric unit relative to the eye to switch to inspection by one of the first optometric portion and the second optometric portion.

19 Claims, 13 Drawing Sheets

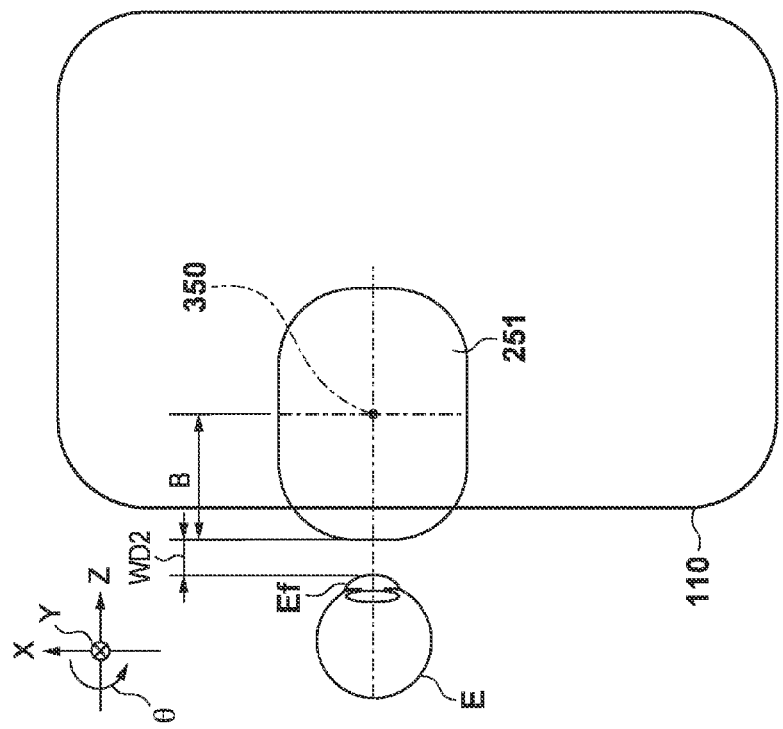
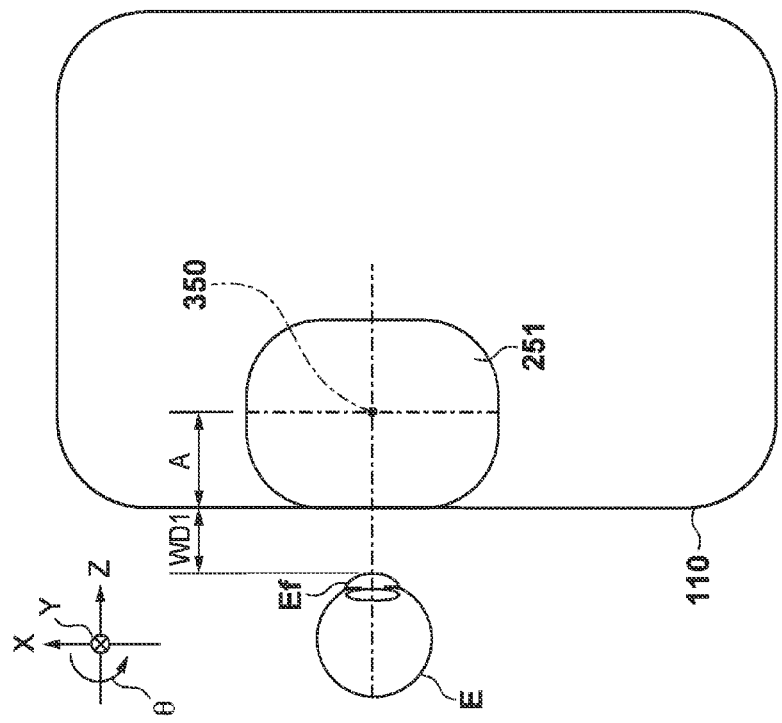

OPHTHALMIC APPARATUS

BACKGROUND OF THE INVENTION

1. Field of the Invention

The present invention relates to an ophthalmic apparatus.

2. Description of the Related Art

As an ophthalmic apparatus which inspects a plurality of eye characteristics of an eye to be examined, there is known an apparatus which includes an eye pressure measurement unit which measures an eye pressure without contact and an ocular refractive power measurement unit which measures an ocular refractive power, and performs measurement by switching the units (Japanese Patent Laid-Open Nos. 2007-289663 and 2010-148589).

In each of the arrangements disclosed in Japanese Patent Laid-Open Nos. 2007-289663 and 2010-148589, the eye pressure measurement unit and the ocular refractive power measurement unit are vertically stacked on each other. The operating distance at the time of measurement of an eye pressure is shorter than that at the time of measurement of an ocular refractive power. That is, the measurement unit performs eye pressure measurement at a position nearer to the eye to be examined. In the above arrangement, therefore, when switching the measurement modes, it is necessary to move the eye pressure measurement unit and the ocular refractive power measurement unit in the back-and-forth direction (the direction to change the operating distance) as well as moving the units in the vertical direction to switch the units. This prolongs the switching time.

The present invention has been made in consideration of the above problem and provides an ophthalmic apparatus which can shorten the optometry switching time and optometry time.

SUMMARY OF THE INVENTION

According to one aspect of the present invention, there is provided an ophthalmic apparatus which is configured to inspect a plurality of eye characteristics of an eye to be examined which is fixed by a face support unit, the apparatus comprising: an optometric unit configured to include a first optometric portion including a first optical system for inspecting a first eye characteristic of the eye, a second optometric portion including a second optical system for inspecting a second eye characteristic different from the first eye characteristic, and a switching unit which includes an optical element commonly used by the first optometric portion and the second optometric portion and is configured switch an optical path to one of the first optometric portion and the second optometric portion by changing a direction of the optical element relative to the eye; and a changing unit configured to change a direction of the optometric unit relative to the eye to switch to inspection by one of the first optometric portion and the second optometric portion.

The present invention can shorten the optometry switching time and optometry time.

Further features of the present invention will become apparent from the following description of exemplary embodiments (with reference to the attached drawings).

BRIEF DESCRIPTION OF THE DRAWINGS

FIGS. 13A and 13B are plan views showing the relative positional relationship between the rotating unit on the optometric unit and an eye to be examined.

DESCRIPTION OF THE EMBODIMENTS (First Embodiment)

Figure 1:
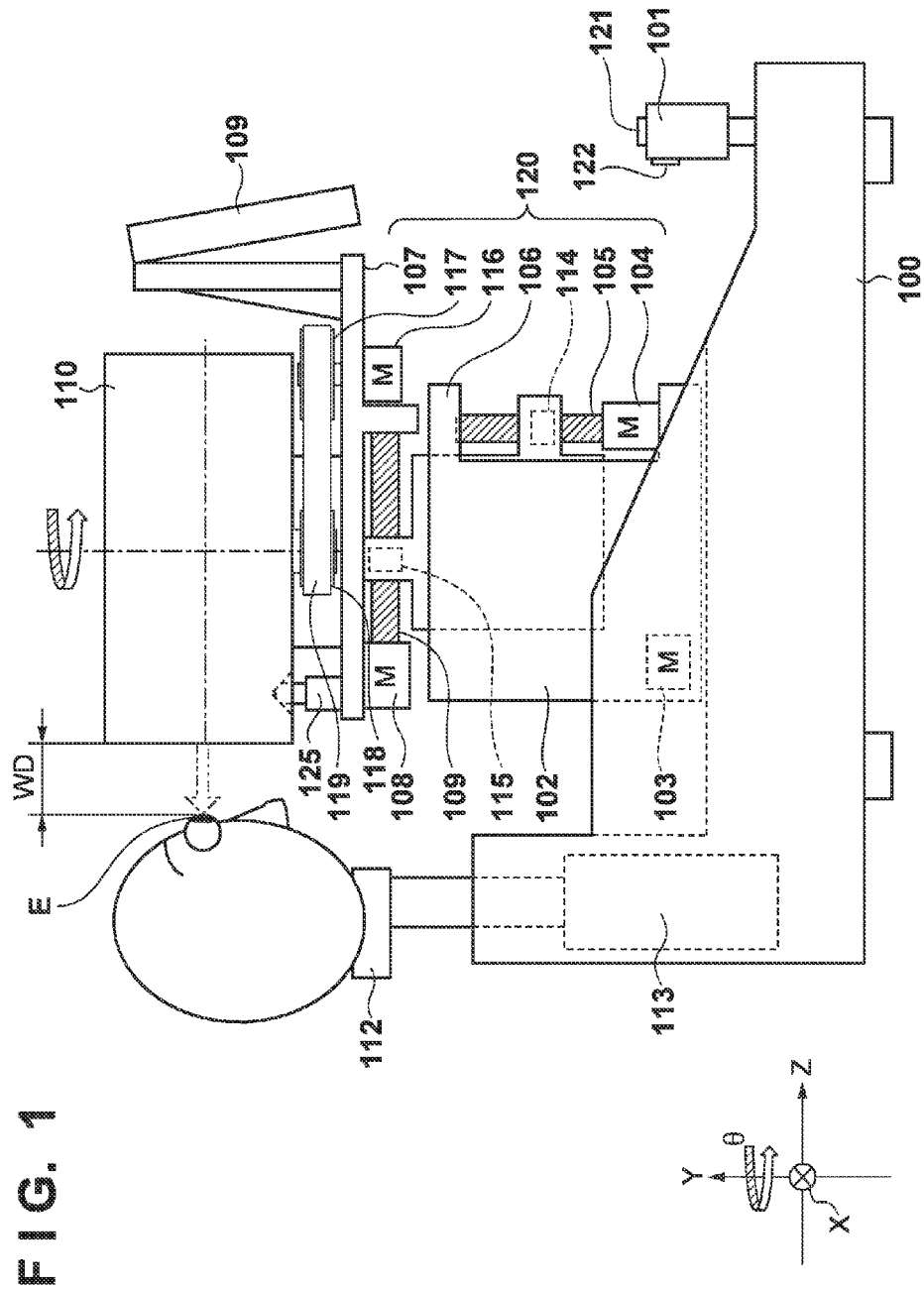
FIG. 1 is a view showing the schematic arrangement of an ophthalmic apparatus according to an embodiment.

An ophthalmic apparatus according to an embodiment of the present invention will be described in detail with reference to the accompanying drawings. FIG. 1 is a view showing the schematic arrangement of the ophthalmic apparatus according to the embodiment. The ophthalmic apparatus includes a base 100 (apparatus fixing portion) and a chin rest 112 for supporting the face of an object. The chin rest 112 is provided on the base 100 (apparatus fixing portion). The ophthalmic apparatus also includes a driving unit 120 provided on the base 100, a joystick 101 as an operation member, a display unit 109, and an optometric unit 110 (measurement unit) attached to the driving unit 120. The driving unit 120 includes driving mechanisms corresponding to the respective axes of the optometric unit 110 to move it in the X, Y, Z, and Θ directions.

(Movement in X-Axis Direction)

A frame 102 can move in the horizontal direction (to be referred to as the X-axis direction hereinafter) relative to the base 100. A driving mechanism in the X-axis direction includes an X-axis driving motor 103 fixed on the base 100, a lead screw (not shown) coupled to a motor output shaft, and a nut (not shown) which is fixed to the frame 102 and can move on the lead screw in the X-axis direction. As the X-axis driving motor 103 rotates, the frame 102 moves in the X-axis direction through the lead screw and the nut.

(Movement in Y-Axis Direction)

A frame 106 can move in the vertical direction (to be referred to as the Y-axis direction hereinafter) relative to the frame 102. A driving mechanism in the Y-axis direction includes a Y-axis driving motor 104 fixed on the frame 102, a lead screw 105 coupled to a motor output shaft, and a nut 114 which is fixed to the frame 106 and can move on the lead screw in the Y-axis direction. As the Y-axis driving motor 104 rotates, the frame 106 moves in the Y-axis direction through the lead screw and the nut.

(Movement in Z-Axis Direction)

A frame 107 can move in the back-and-forth direction (to be referred to as the Z-axis direction hereinafter) relative to the frame 106. A driving mechanism in the Z-axis direction includes a Z-axis driving motor 108 fixed on the frame 107, a lead screw 109 coupled to a motor output shaft, and a nut 115 which is fixed to the frame 106 and can move on the lead screw in the Z-axis direction. As the Z-axis driving motor 108 rotates, the frame 107 moves in the Z-axis direction through the lead screw and the nut.

(Rotation in Θ-Axis Direction)

The optometric unit 110 can move in the rotational direction (to be referred to as the Θ-axis direction hereinafter) relative to the frame 107. A driving mechanism in the Θ-axis direction includes a Θ-axis driving motor 116 fixed on the frame 107 and a pulley 117 coupled to a motor output shaft. The driving mechanism in the Θ-axis direction includes a pulley 118 coupled to the optometric unit 110 and a belt 119 coupled to the pulley 117 and the pulley 118. As the Θ-axis driving motor 116 rotates, the optometric unit 110 rotationally moves around the rotation axis (Θ-axis direction) relative to the base 100 through the pulley 117, the belt 119, and the pulley 118.

(Positioning Stopper)

A stopper 125 (positioning member) for positioning the optometric unit is fixed on the frame 107. The stopper 125 has a wedge-shaped distal end. The stopper 125 is driven in the vertical direction to be inserted into a positioning groove portion provided in the lower portion of the optometric unit 110. The Θ-axis driving motor 116 is driven to rotationally move the optometric unit 110 in the Θ-axis direction. The stopper 125 is then inserted into the groove portion to position and fix the optometric unit 110 at a predetermined position.

(LCD Monitor)

The examiner-side end portion of the frame 107 is provided with an LCD monitor as the display unit 109 for observing an eye E to be examined as an inspection target of the optometric unit 110.

(Chin Rest)

When performing optometry, the examiner can fix the position of the eye to be examined by letting the object rest his/her chin on the chin rest 112 and pressing his/her forehead against the forehead rest portion of a face support unit (not shown) fixed to the base 100. It is possible to move the position of the chin rest 112 by driving a chin rest driving motor 113. It is possible to raise or lower the chin rest 112 so as to adjust its position by driving the chin rest driving motor 113.

(Joystick)

The base 100 is provided with the joystick 101 as an operation member for positioning the optometric unit 110 relative to the eye E as an inspection target and an optometry switching button 122. The examiner instructs the driving direction, driving amount, and driving speed of the driving unit 120 by tilting/operating the joystick 101. Upon positioning (aligning) the optometric unit 110 relative to an eye to be examined as an inspection target, the examiner executes measurement by pressing a measurement start button 121 provided on the joystick 101.

(Optical System)

Figure 2:
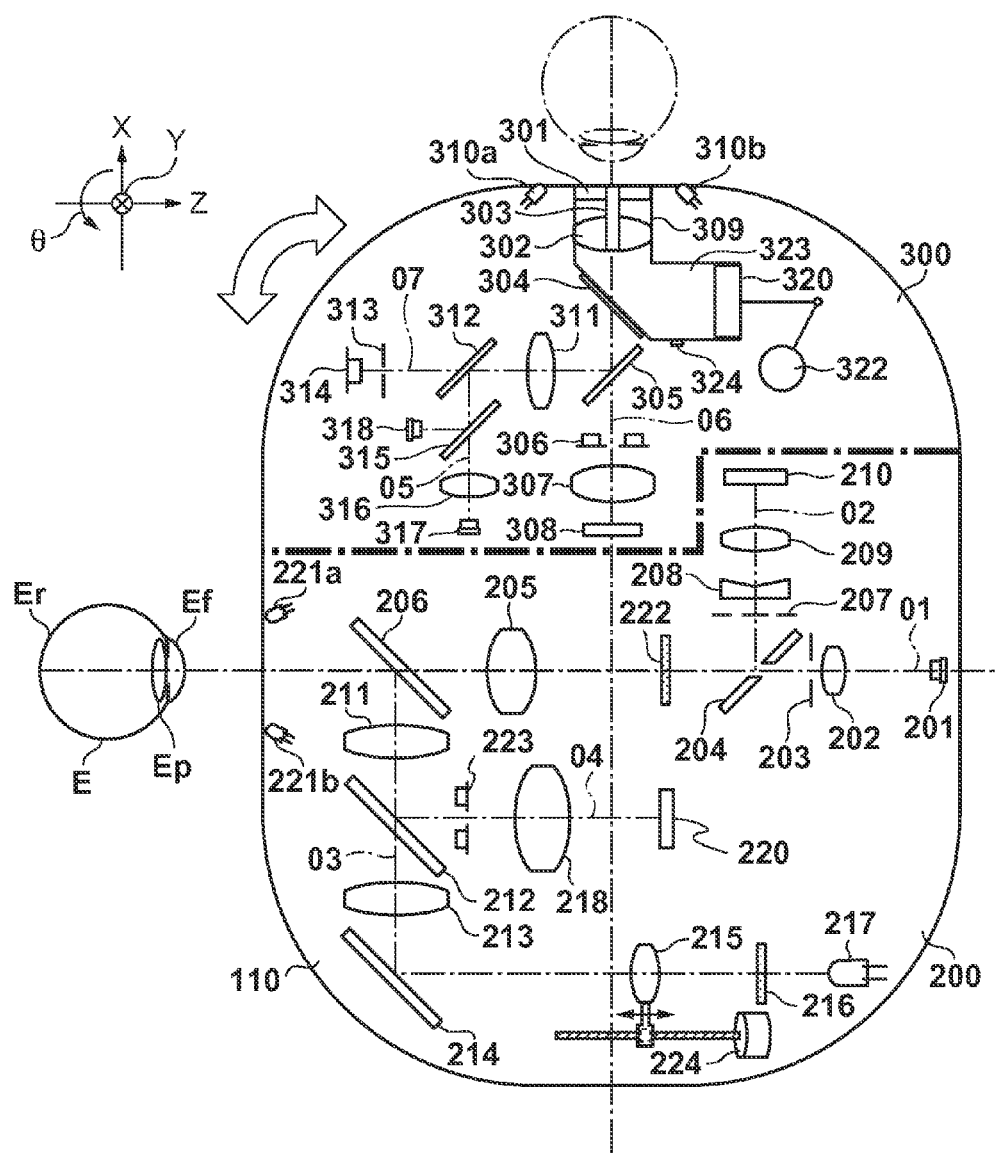
FIG. 2 is a view showing the arrangement of the optical system of the optometric unit of the ophthalmic apparatus according to the embodiment.

The optometric unit 110 includes an optical system for measurement, observation, and the like of an eye to be examined as an inspection target. FIG. 2 shows the arrangement of an optical system in the optometric unit 110 in the ophthalmic apparatus according to this embodiment. The optical system in the optometric unit 110 includes a first optical system 200 (first optometric unit) for inspecting the first eye characteristic and a second optical system 300 (second optometric unit) for inspecting the second eye characteristic different from the first eye characteristic of the eye to be examined. The driving mechanism (changing unit) in the Θ-axis direction changes the direction of the optometric unit 110 for an eye to be examined to switch between inspection by the first optometric portion and inspection by the second optometric portion.

The first optical system 200 is an optical system for inspecting the ocular refractive power of the eye to be examined. A projection lens 202, a stop 203 almost conjugate to a pupil Ep of the eye E, a perforated mirror 204, and a lens 205 are arranged on an optical path 01 extending from an ocular refractive power measurement light source 201 for emitting light with a wavelength of 880 nm to the eye E. The dichroic mirror 206 totally reflects infrared and visible light with wavelengths of 880 nm or more from the eye E side, and partly reflects a light beam with a wavelength of 880 nm or more.

A stop 207 which includes an annular slit and is almost conjugate to the pupil Ep, a light beam spectral prism 208, a lens 209, an image sensor 210 are sequentially disposed on an optical path 02 in the reflecting direction of the perforated mirror 204.

The above optical system is used for ocular refractive power measurement, in which the stop 203 restricts the light beam emitted from the ocular refractive power measurement light source 201. The projection lens 202 performs primary image formation in front of the lens 205. The resultant light beam is transmitted through the lens 205 and the dichroic mirror 206 and projected onto the pupil center of the eye E.

The reflected light of the projected light beam passes through the pupil center and enters the lens 205 again. The incident light beam is transmitted through the lens 205 and then reflected by the periphery of the perforated mirror 204.

The stop 207 almost conjugate to the pupil Ep of the eye to be examined and the light beam spectral prism 208 pupil-split the reflected light beam. The resultant light beam is projected as a ring image on the light-receiving surface of the image sensor 210. If the eye E is a normal-sighted eye, this ring image becomes a predetermined circle. If the eye E is a near-sighted eye, the projected image becomes a circle smaller than that originating from the normal-sighted eye. If the eye E is a far-sighted eye, the projected image becomes a circle larger than that originating from the normal-sighted eye. If the eye E has astigmatism, the ring image becomes an ellipse, with the angle defined by the horizontal axis and the ellipse representing an astigmatic axis angle. A refractive power is obtained based on this elliptic coefficient.

On the other hand, a visual fixation target projection optical system and an alignment light-receiving optical system used for both anterior ocular segment observation and alignment detection are arranged in the reflection direction of the dichroic mirror 206.

A lens 211, a dichroic mirror 212, a lens 213, a folding mirror 214, a lens 215, a visual fixation target 216, and a visual fixation target illumination light source 217 are sequentially arranged on an optical path 03 of the visual fixation target projection optical system.

At the time of visual fixation guidance, the projection light beam emitted from the visual fixation target illumination light source 217 in an ON state illuminates the visual fixation target 216 from the back side. The light beam is then projected onto a fundus Er of the eye E through the lens 215, the folding mirror 214, the lens 213, the dichroic mirror 212, and the lens 211.

Note that a visual fixation target guide motor 224 can move the lens 215 in the optical axis direction so as to implement a fogging state by performing visual fixation guidance for the eye E.

The alignment prism stop 223 which is inserted and removed by an alignment prism stop insertion/removal solenoid 411, an imaging lens 218, and an image sensor 220 are sequentially arranged on an optical path 04 in the reflecting direction of the dichroic mirror 212.

Inserting and removing the alignment prism stop 223 can perform alignment when the alignment prism stop 223 is located on the optical path 04 and can perform anterior ocular segment observation or transillumination observation when the alignment prism stop 223 is retracted from the optical path.

Figure 3A:
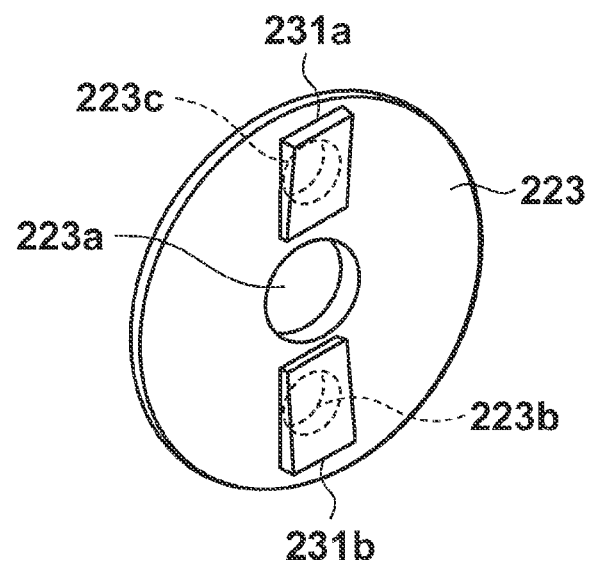
FIGS. 3A and 3B are perspective views each showing an alignment prism stop of the ophthalmic apparatus according to the embodiment.

FIG. 3A shows the shape of the alignment prism stop 223. The disk-like stop plate is provided with three aperture portions 223a, 223b, and 223c. Alignment prisms 231a and 231b which transmit only light beams near a wavelength of 880 nm are bonded to the aperture portions 223a and 223b on the dichroic mirror 212 side.

Referring back to FIG. 2, anterior ocular segment illumination light sources 221a and 221b having a wavelength of about 780 nm are arranged diagonally in front of the anterior ocular segment of the eye E. The light beams of anterior ocular segment images of the eye E illuminated by the anterior ocular segment illumination light sources 221a and 221b are formed into images on the light-receiving sensor surface of the image sensor 220 via the dichroic mirror 206, the lens 211, the dichroic mirror 212, and the aperture portion 223a in the center of the alignment prism stop.

The light source used for alignment detection is also used as the ocular refractive power measurement light source 201. At the time of alignment, a diffuser panel insertion/removal solenoid 410 inserts a translucent diffuser panel 222 in an optical path.

The position at which the diffuser panel 222 is inserted is almost the primary imaging position of the projection lens 202 of the ocular refractive power measurement light source 201 and also coincides with the focal position of the lens 205. With this arrangement, an image of the ocular refractive power measurement light source 201 is temporarily formed on the diffuser panel 222. This image becomes a secondary light source and is projected from the lens 205 as a thick parallel light beam toward the eye E.

This parallel light beam is reflected by a cornea Ef of the eye to be examined and forms a bright spot image. The dichroic mirror 206 partly reflects this light beam again. This light beam is reflected by the dichroic mirror 212 through the lens 211, transmitted through the aperture portion 223a and alignment prisms 231a and 231b of the alignment prism stop, and focused by the imaging lens 218 to be formed into an image on the image sensor 220.

Light beams having a wavelength of 780 nm or more from the anterior ocular segment illumination light sources 221a and 221b pass through the aperture portion 223a in the center of the alignment prism stop 223. The anterior ocular segment image reflected light beams illuminated by the anterior ocular segment illumination light sources 221a and 221b propagate along the observation optical system like the path of a reflected light beam from the cornea Ef. These light beams are formed into images on the image sensor 220 by the imaging lens 218 through the aperture portion 223a of the alignment prism stop 223.

The light beam transmitted through the alignment prism 231a is refracted downward, and the light beam transmitted through the alignment prism 231b is refracted upward. It is possible to align the eye E in accordance with the positional relationship between these light beams passing through the stop.

While the alignment prism stop 223 and the cornea stop are retracted from the optical path 04, the dichroic mirror 206 reflects part of a light beam from the pupil area illuminated by the light beam emitted from the ocular refractive power measurement light source 201 and reflected by the fundus Er. This light beam is reflected by the dichroic mirror 212 through the lens 211. The imaging lens 218 then projects the light beam onto the image sensor 220. This light beam allows the observation of the eye E.

A second optical system 300 is an optical system for inspecting the eye pressure of an eye to be examined. On a light-receiving optical path and alignment detection optical path 06 of an observation optical system for the eye E, a nozzle 303 is disposed on the central axis of a plane parallel glass plate 301 and objective lens 302. An air chamber 323, an observation window 304, a dichroic mirror 305, a prism stop 306, an imaging lens 307, and an image sensor 308 are sequentially arranged behind the objective lens 302.

An objective lens barrel 309 supports the plane parallel glass plate 301 and the objective lens 302. Extraocular illumination light sources 310a and 310b for illuminating the eye E are arranged outside the objective lens barrel 309.

A relay lens 311, a half mirror 312, an aperture 313, and a light-receiving element 314 are arranged, in the reflecting direction of the dichroic mirror 305, on an optical path 07 of a deformation detection light-receiving optical system when the cornea Ef deforms in the visual axis direction. Note that the aperture 313 is disposed at a position at which it is conjugate to a cornea reflected image of an eye pressure measurement light source 317 (to be described later) at the time of predetermined deformation.

The relay lens 311 is designed to form a cornea reflected image almost equal in size to the aperture 313 when a cornea Ec deforms into a predetermined shape.

A half mirror 315 and a projection lens 316 are arranged, in the incident direction of the half mirror 312, on an optical path 05 of a measurement light source projection optical system for measuring the deformation of the cornea Ef. In addition, an eye pressure measurement light source 317 formed from a near-infrared LED used for both measurement and alignment for the eye E is disposed on the above optical path. Furthermore, a visual fixation light source 318 formed from an LED for visual fixation by an object is disposed in the incident direction of the half mirror 315.

A piston 320 is fitted in the objective lens barrel 309 forming part of the air chamber 323. A solenoid 322 drives the piston 320. Note that a pressure sensor 324 for monitoring an internal pressure is arranged in the air chamber 323.

(External Dimensions)

Figure 4A:
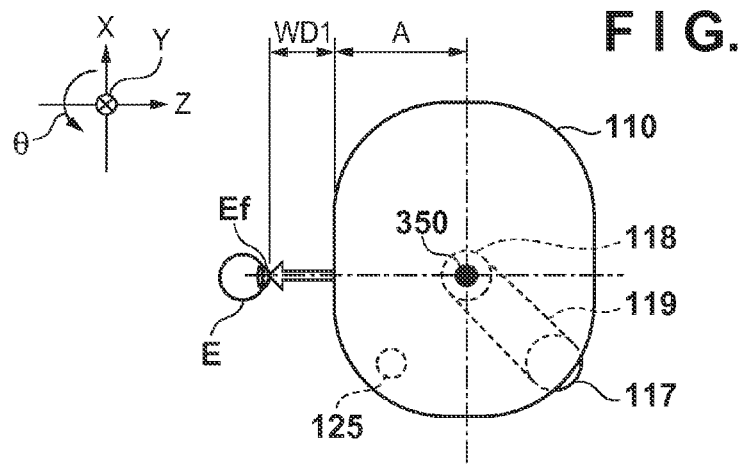
FIGS. 4A to 4C are plan views of the optometric unit of the ophthalmic apparatus according to the embodiment.
Figure 4B:
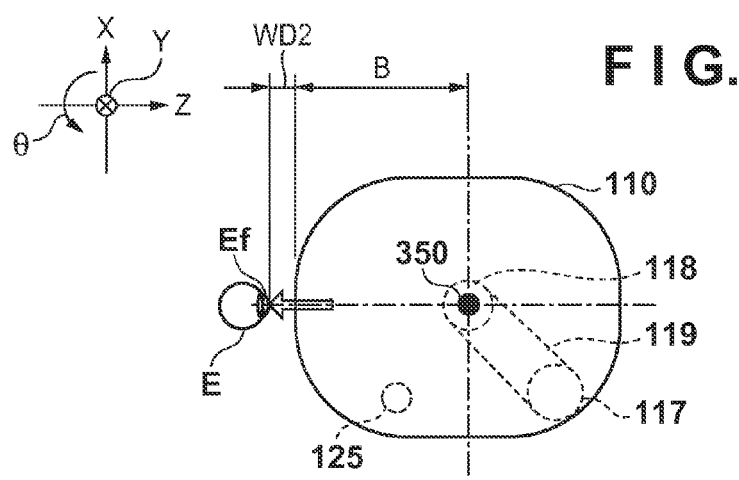
Figure 4C:
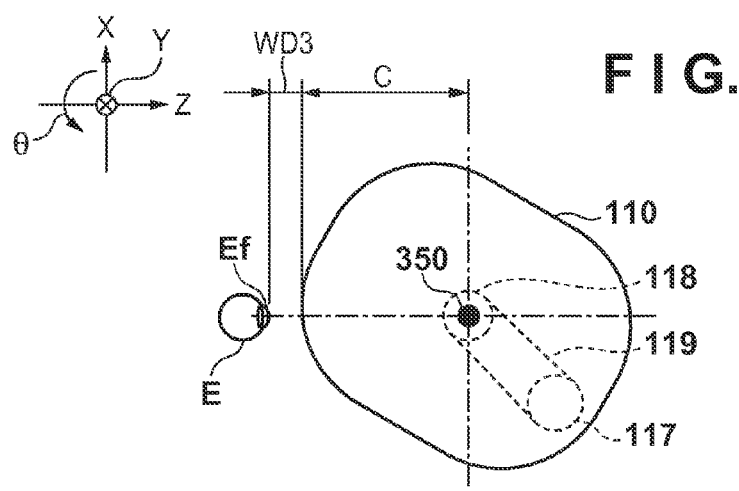

FIGS. 4A to 4C are plan views of the optometric unit 110. FIG. 4A shows the positional relationship between the optometric unit 110 and the eye E at the time of measurement of an ocular refractive power by the first optical system 200. FIG. 4B shows the positional relationship between the optometric unit 110 and the eye E at the time of measurement of an eye pressure by the second optical system 300. Let WD1 be an operating distance at the time of measurement of an ocular refractive power by the first optical system 200, that is, the distance from a cornea vertex Ef of the eye E to the first optical system output-side end portion of the optometric unit 110, and A be the distance from a center of rotation 350 to the first optical system output-side end portion of the optometric unit 110. In addition, let WD2 be an operating distance at the time of measurement of an eye pressure by the second optical system 300, that is, the distance from the cornea vertex Ef of the eye E to the second optical system output-side end portion of the optometric unit 110, and B be the distance from the center of rotation 350 to the second optical system output-side end portion of the optometric unit 110. In this case, the optometric unit 110 and the center of rotation 350 are configured to satisfy WD1+A=WD2+B. FIG. 4C shows the positional relationship between the eye E and the optometric unit 110 during rotational movement. The external dimensions of the optometric unit 110 except for the first and second optical system output-side end portions are configured such that an external dimension C from the center of rotation 350 keeps a distance WD3 at which the optometric unit 110 does not come into contact with any protruding portion of the object during rotational movement.

(System Block Diagram)

Figure 5:
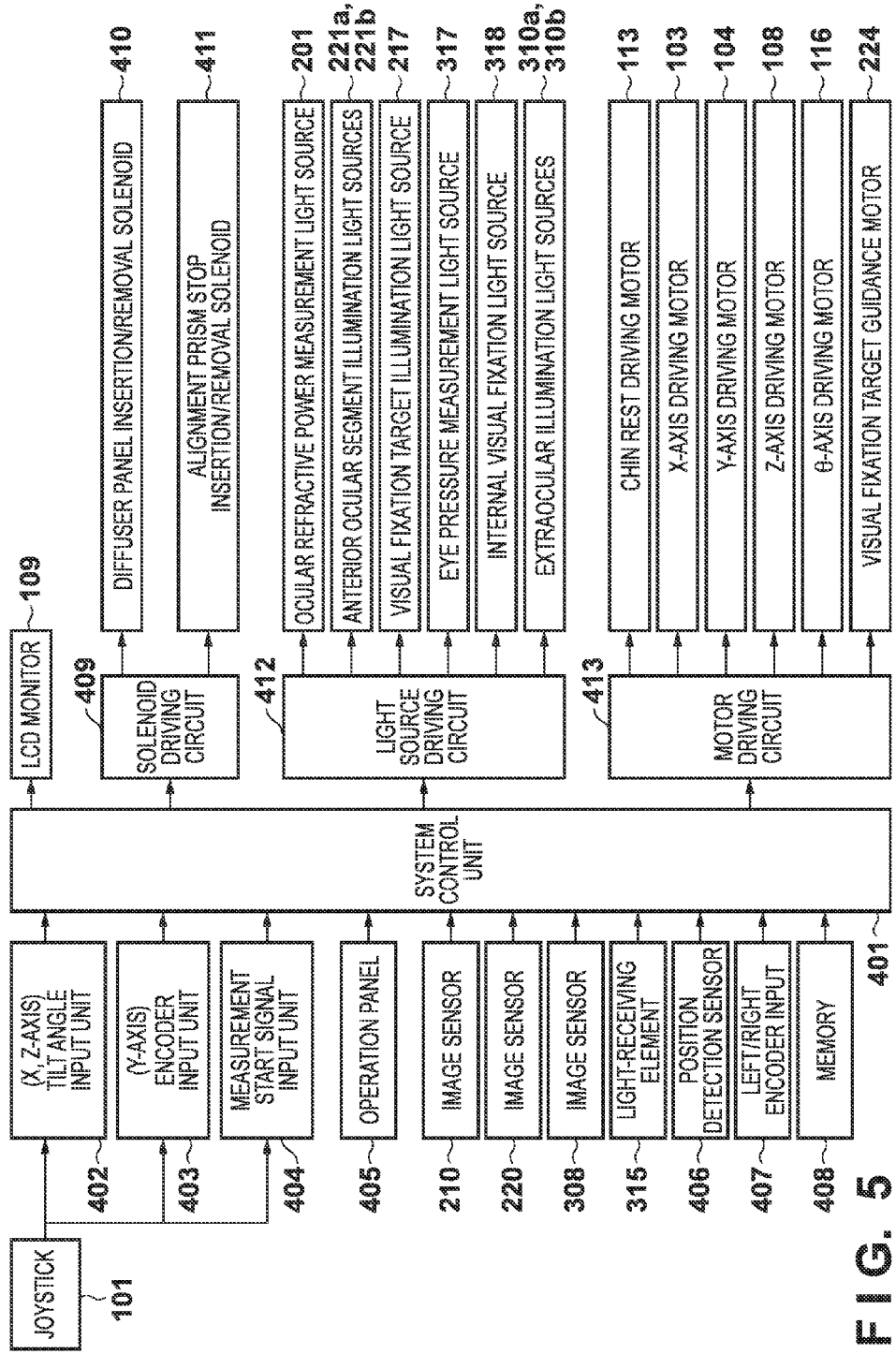
FIG. 5 is a block diagram showing the arrangement of the control system of the ophthalmic apparatus according to the embodiment.

FIG. 5 is a system block diagram of the ophthalmic apparatus. A system control unit 401 controls the overall system. The system control unit 401 includes a program storage unit and a data storage unit storing data for correcting eye pressure values, ocular refractive power values, and the like. The system control unit 401 also includes an input/output control unit which controls input/output operation with various types of devices and an arithmetic processing unit which computes the data obtained from various types of devices.

A tilt angle input unit 402, an encoder input unit 403, and a measurement start signal input unit 404 are connected to the system control unit 401. The system control unit 401 receives instructions (signals) from the joystick 101 for positioning the optometric unit 110 to the eye E and starting measurement via the tilt angle input unit 402, the encoder input unit 403, and the measurement start signal input unit 404. The tilt angle input unit 402 detects tilt angles when the examiner tilts the joystick 101 back and forth and left and right and inputs detected tilt angles to the system control unit 401. The encoder input unit 403 accepts encoder signals from various types of driving motors when the examiner operates the joystick 101 to rotate the respective types of driving motors, and inputs the signals to the system control unit 401. The measurement start signal input unit 404 accepts a signal transmitted when the examiner presses the measurement start button of the joystick 101, and inputs the signal to the system control unit 401.

In addition, a print button, a chin rest up/down button, and the like are arranged on an operation panel 405 on the base 100. When the examiner performs button input operation, the panel notifies the system control unit 401 of a corresponding signal. Furthermore, signals from the respective types of position detection sensors 406 (detection units) are notified to the system control unit 401 when the sensors are turned on.

A memory 408 stores the anterior ocular segment image of the eye E captured by the image sensor 220. The system control unit 401 extracts the pupil and cornea reflected images of the eye E from the image stored in the memory 408 and performs alignment detection. In addition, the anterior ocular segment image of the eye E captured by the image sensor 220 is combined with characters and graphic data to display the anterior ocular segment image and measurement values on the LCD monitor (display unit 109).

The memory 408 stores the ring image for ocular refractive power calculation captured by the image sensor 210.

The system control unit 401 issues commands via a solenoid driving circuit 409 to control the driving of the solenoids 410 to 412.

In addition, the X-axis driving motor 103, the Y-axis driving motor 104, the Z-axis driving motor 108, the chin rest driving motor 113, the Θ-axis driving motor 116, a face support driving motor 131, and the visual fixation target guidance motor 224 are connected to a motor driving circuit 413. The motor driving circuit 413 accepts commands from the system control unit 401 and drives the respective types of motors.

The ocular refractive power measurement light source 201, the anterior ocular segment illumination light sources 221a and 221b for ocular refractive power measurement, the visual fixation target illumination light source 217, the eye pressure measurement light source 317, the visual fixation light source 318, and the extraocular illumination light sources 310a and 310b for eye pressure measurement are connected to a light source driving circuit 412. The light source driving circuit 412 accepts commands from the system control unit 401 and controls ON/OFF operation and light amount changing operation of the respective types of light sources.

The operation of the apparatus having the above arrangement will be described.

(Ocular Refractive Power Measurement)

Figure 6A:
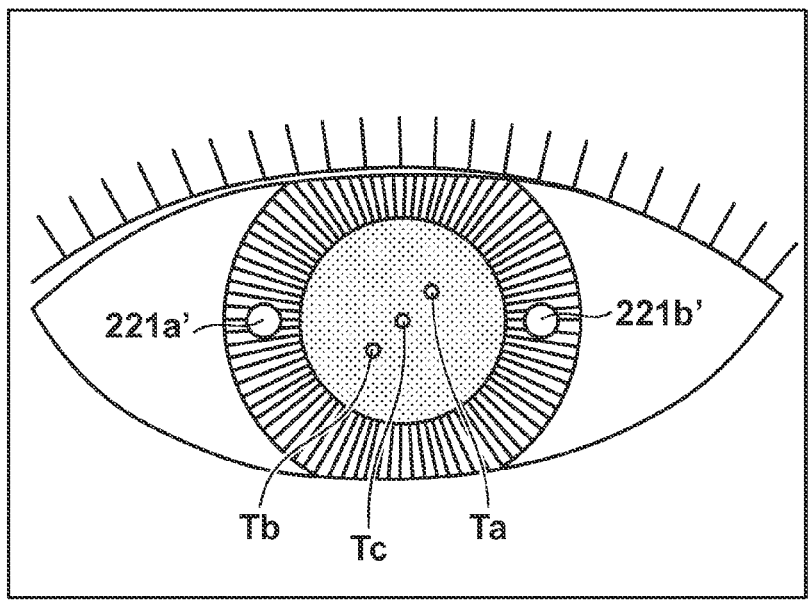
FIGS. 6A and 6B are views for explaining the anterior ocular segment images captured by the ophthalmic apparatus according to the embodiment.

As shown in FIG. 6A, at the time of alignment, the aperture portions 223a, 223b, and 223c of the alignment prism stop 223 and the alignment prisms 231a and 231b split the cornea bright spot formed by the cornea Ef. The image sensor 220 captures, as index images Ta, Tb, and Tc, the cornea bright spots, the eye E illuminated by the anterior ocular segment illumination light sources 221a and 221b, and bright spot images 221a' and 221b' of the anterior ocular segment illumination light sources 221a and 221b.

Alignment is executed in two steps, namely rough alignment of performing rough positioning and fine alignment of performing fine positioning.

Rough alignment uses the eye E and the bright spot images 221a' and 221b' of the anterior ocular segment illumination light sources 221a and 221b. Upon detecting the eye E and the bright spot images 221a' and 221b', the system control unit 401 controls the motor driving circuit 413. The system control unit 401 then drives the optometric unit 110 up and down and left and right so as to align the bright spot images 221a' and 221b' with the pupil center of the eye E in the X and Y directions.

The system control unit 401 then calculates Z-coordinates and areas of the bright spot images 221a' and 221b' and drives the optometric unit 110 in the back-and-forth direction so as to align the images with a predetermined position, thereby performing rough positioning.

Fine alignment uses the index images Ta, Tb, and Tc. Upon detecting the three bright spots Ta, Tb, and Tc, the system control unit 401 controls the motor driving circuit 413. The system control unit 401 drives the optometric unit 110 up and down and left and right so as to align the middle bright spot Tc with the center of the eye E. The system control unit 401 drives the optometric unit 110 back and forth so as to align the bright spots Ta and Tb with the bright spot Tc in the vertical direction, and completes the alignment upon aligning the three cornea bright spots Ta, Tb, and Tc with each other in the vertical direction.

To measure an ocular refractive power, the system control unit 401 retracts the diffuser panel 222, which has been inserted in the optical path 01 for automatic alignment, from the optical path 01. The system control unit 401 adjusts the light amount of the ocular refractive power measurement light source 201 and projects a measurement light beam on the fundus Er of the eye E.

The image sensor 210 receives reflected light from the fundus along the optical path 02. The stop 207 projects the captured fundus image into a ring image owing to the refractive power of the eye to be examined. The memory 408 stores this ring image.

The system control unit 401 calculates the barycentric coordinates of the ring image stored in the memory 408 and obtains an ellipse equation by a known method. The system control unit 401 calculates the major and minor axes and major-axis gradient of the obtained ellipse and calculates the ocular refractive power of the eye E.

Note that ocular refractive powers corresponding to the major and minor axes of the obtained ellipse and the relationship between the angle of the ellipse axis and the astigmatic axis on the light-receiving surface of the image sensor 210 have been corrected in advance in the manufacturing process of the apparatus.

The system control unit 401 drives the visual fixation target guidance motor 224 via the motor driving circuit 413 to move the lens 215 to a position corresponding to a refractive power corresponding to the obtained ocular refractive power, and presents the eye E with the visual fixation target 216 with a degree of refraction corresponding to the degree of refraction of the eye E.

Subsequently, the system control unit 401 moves the lens 215 to a predetermined distance, fogs the visual fixation target 216, and turns on the measurement light source again to measure a refractive power. It is possible to obtain the final measurement value, at which the refractive power becomes stable, by repeating measurement of a refractive power, fogging of the visual fixation target 216, and measurement of a refractive power in this manner.

(Eye Pressure Measurement)

Figure 3B:
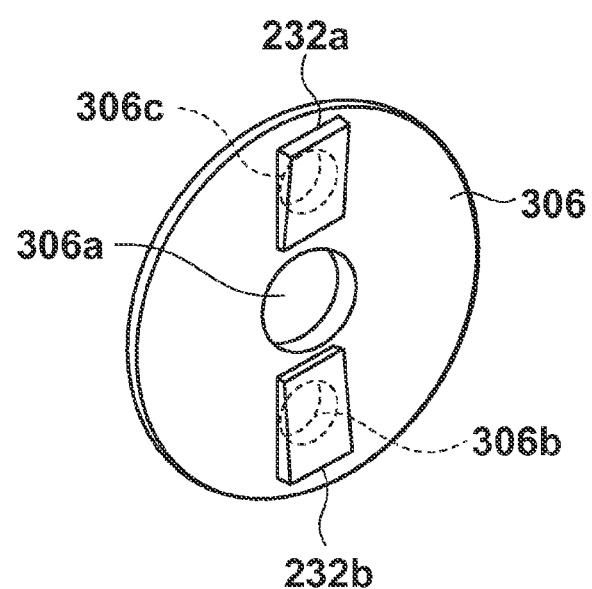
Figure 6B:
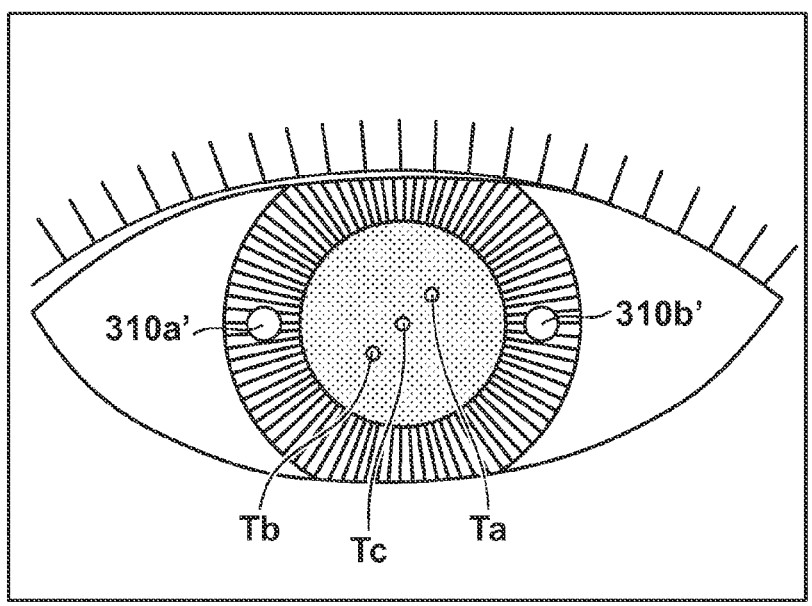

As shown in FIG. 6B, at the time of alignment for eye pressure measurement, aperture portions 306a, 306b, and 306c of the prism stop 306 and prisms 232a and 232b shown in FIG. 3B split the cornea bright spot formed by the cornea Ef. The image sensor 308 captures, as index images Ta, Tb, and Tc, the cornea bright spots, the eye E illuminated by the extraocular illumination light sources 310a and 310b, the cornea bright spots, the eye E illuminated by the extraocular illumination light sources 310a and 310b, and bright spot images 310a' and 310b' of the extraocular illumination light sources 310a and 310b. The following operation is the same as that performed at the time of alignment for ocular refractive power measurement.

The system control unit 401 performs eye pressure measurement after the completion of alignment. The system control unit 401 drives the solenoid 322. The piston 320 raised by the solenoid 322 compresses the air in the air chamber 323 to jet an air pulse from the nozzle 303 to the cornea Ef of the eye E.

The pressure signal detected by the pressure sensor 324 of the air chamber 323 and the light reception signal from the light-receiving element 314 are output to the system control unit 401. The system control unit 401 then calculates an eye pressure value from the peak value of the light reception signal and the pressure signal at this time.

(Explanation of Operation in Automatic Driving)

Figure 7:
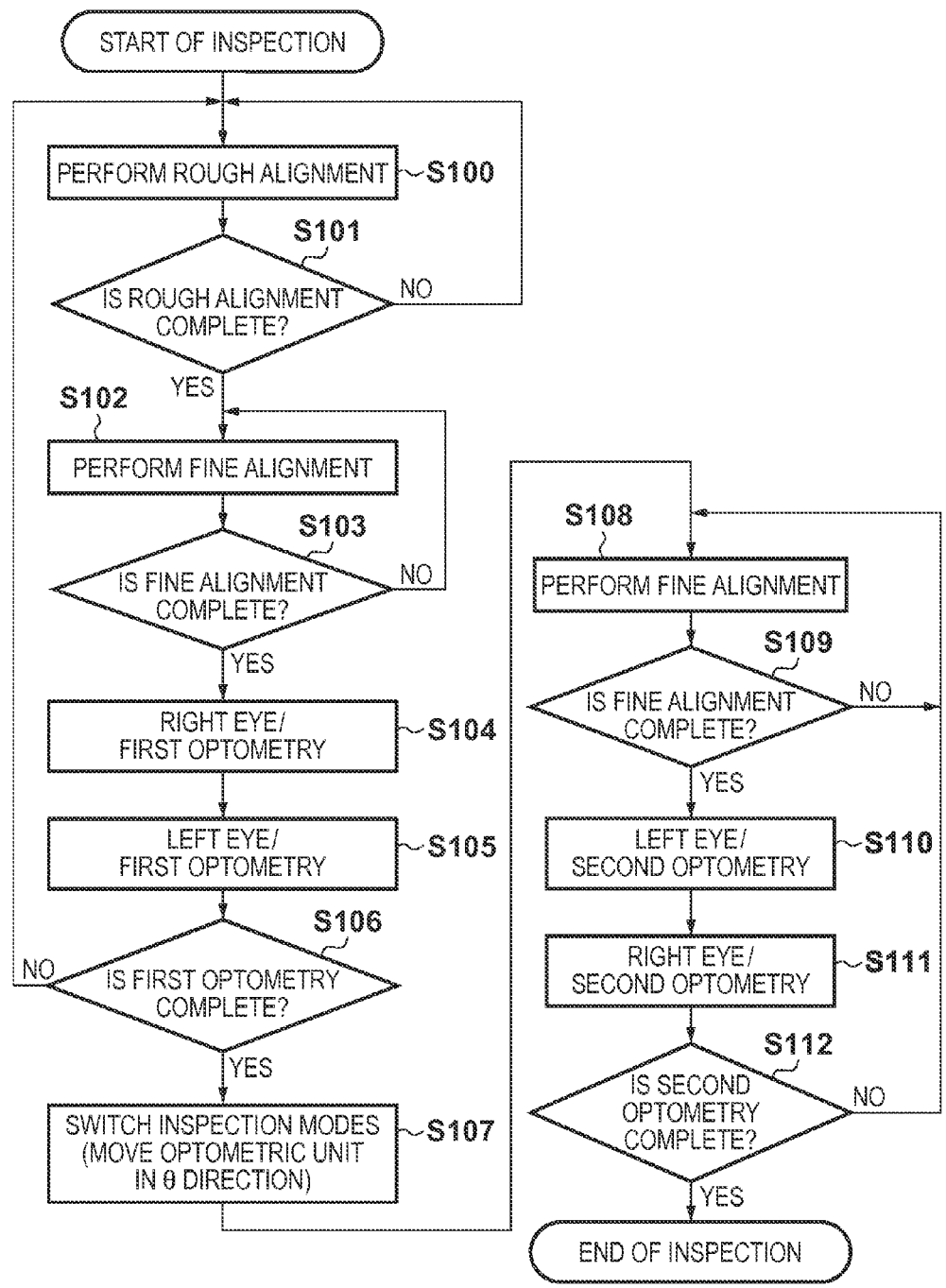
FIG. 7 is a flowchart for explaining the operation of the ophthalmic apparatus at the time of optometry according to the embodiment.

Operation in automatic driving as operation at the time of optometry in the ophthalmic apparatus having the above arrangement will be described with reference to the flowchart of FIG. 7 and the operation charts of FIGS. 8A to 8C.

When the examiner 140 turns on the power supply to start up the ophthalmic apparatus, the ophthalmic apparatus initializes the respective types of devices. First of all, in order to measure the ocular refractive power of a right eye ER to be examined of an object 150, the optometric unit 110 moves to a position to measure the ocular refractive power of the right eye ER, thus completing preparation. In this state, the examiner 140 makes the object 150 rest his/her chin on the chin rest 112 and press his/her forehead against the forehead rest portion (not shown) to fix the eye E. The examiner 140 then selects the full automatic mode by operating a switch (not shown) on the LCD monitor (display unit 109). The examiner 140 sets the pupil center of the right eye ER in the observation range of the LCD monitor (display unit 109) by tilting the joystick 101, as needed. When the examiner presses the measurement start button 121 in this state, the apparatus starts automatic measurement.

When the examiner presses the measurement start button 121, the apparatus starts rough alignment to perform rough positioning for ocular refractive power measurement (step S100). Upon completing the rough alignment (step S101), the apparatus starts fine alignment to perform more precise positioning (step S102).

Figure 8A:
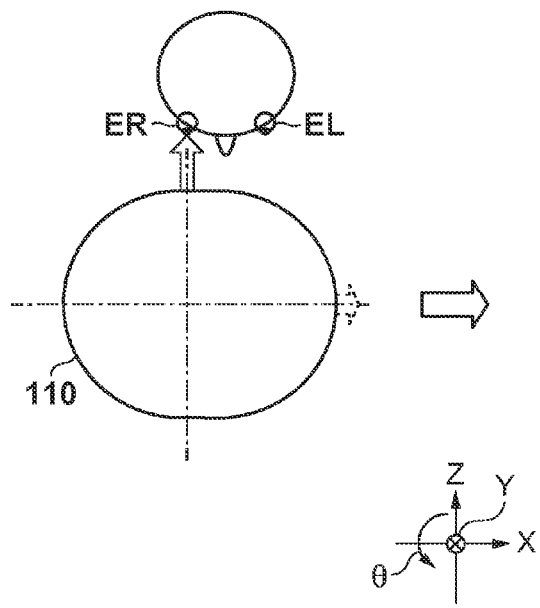
FIGS. 8A to 8D are views for explaining the operation of the optometric unit at the time of optometry by the ophthalmic apparatus according to the embodiment.
Figure 8B:
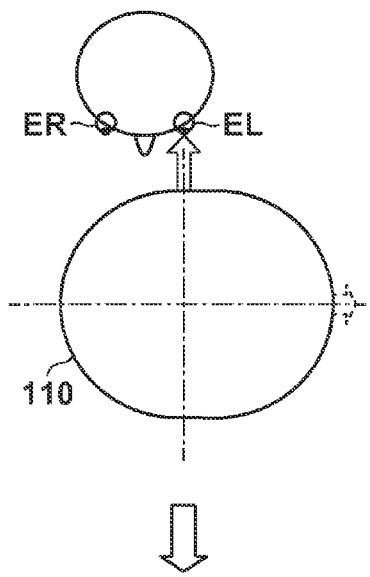

Upon completing the fine alignment (step S103), the apparatus measures the ocular refractive power of the right eye ER of the object a predetermined number of times (step S104 and FIG. 8A: right eye/first optometry). Upon measuring the ocular refractive power of the right eye to be examined, the apparatus moves the optometric unit 110 in the X and Z directions by necessary amounts, and measures the ocular refractive power of a left eye EL to be examined of the object a predetermined number of times (step S105 and FIG. 8B: left eye/first optometry). The apparatus repeats measurement in steps S100 to S105 until performing ocular refractive power measurement a predetermined number of times (NO in step S106). Upon completely measuring the ocular refractive powers of the left and right eyes a predetermined number of times (YES in step S106), the apparatus moves the optometric unit 110 in the Θ direction to switch optometry from ocular refractive power measurement to eye pressure measurement (step S107). At this time, the optometric unit 110 rotationally moves so as not to come into contact with any protruding portion (for example, the nose) of the object. More specifically, the output-side end portion of the eye pressure measurement optical system of the optometric unit 110 rotationally moves from the left ear side to the nose side of the object (FIG. 8C). This makes it possible to perform quick switching operation with only the Θ axis while preventing interference with any protruding portion of the object. In addition, since switching is performed by just rotating operation with only the Θ axis and the distance from the center of rotation to the eye E is constant, the positions of the optometric unit 110 in the X and Y directions are reproduced and an operating distance in the Z direction required for eye pressure measurement can be automatically obtained. This makes it unnecessary to perform rough alignment after switching operation, and can further shorten the optometry time. After switching operation, the apparatus starts fine alignment for the left eye EL of the object (step S108). Upon completing the fine alignment (step S109), the apparatus measures the eye pressure of the left eye EL a predetermined number of times (step S110 and FIG. 8C: left eye/second optometry).

Figure 8D:
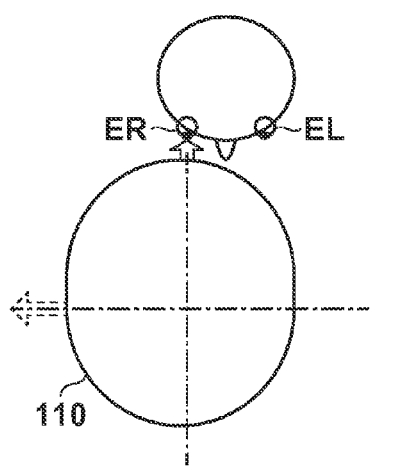
Figure 8C:
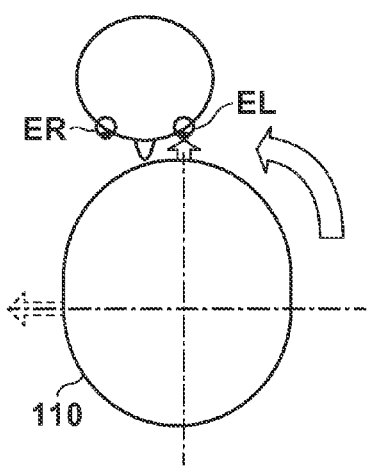

Upon completing eye pressure measurement of the left eye EL, the apparatus moves the optometric unit 110 in the X and Z directions by necessary amounts and measures the eye pressure of the right eye ER a predetermined number of times (step S111 and FIG. 8D: right eye/second optometry). The apparatus repeats processing in steps S108 to S111 until performing eye pressure measurement a predetermined number of times (NO in step S112). Upon completing eye pressure measurement of the left and right eyes a predetermined number of times (YES in step S112), the apparatus terminates the inspection.

(Second Embodiment)

Figure 9A:
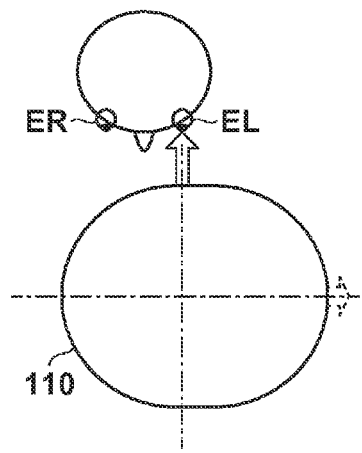
FIGS. 9A to 9D are views for explaining the operation of an optometric unit at the time of optometry by an ophthalmic apparatus according to the second embodiment.
Figure 9B:
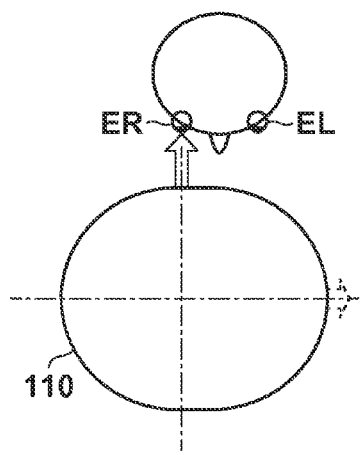
Figure 9B:
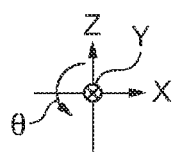
Figure 9D:
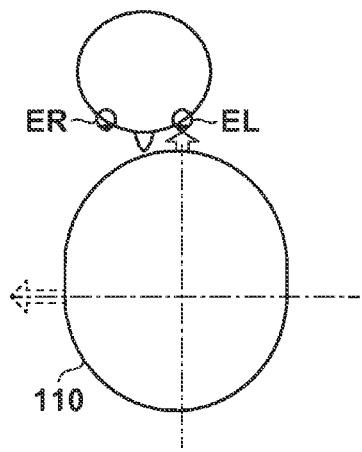
Figure 9C:
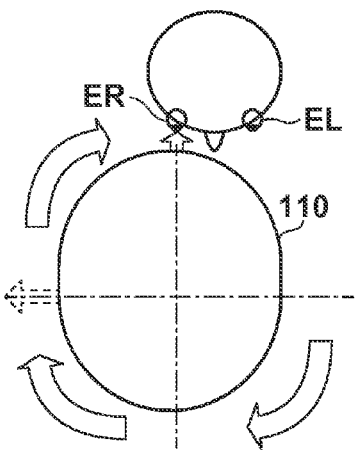

FIGS. 9A to 9D are views for explaining the second embodiment in a case in which ocular refractive power measurement starts from the left eye to be examined. In this case, upon performing ocular refractive power measurement in the order of a left eye EL to be examined and a right eye ER to be examined (FIGS. 9A and 9B), the apparatus moves an optometric unit 110 in the Θ direction to switch optometry from ocular refractive power measurement to eye pressure measurement. At the time of this switching operation, a system control unit 401 rotates the optometric unit 110 to move it from the output-side end portion of the eye pressure measurement optical system to the right ear side so as not to come into contact with any protruding portion (for example, the nose) of the object. This makes it possible to quickly perform switching operation with only the Θ axis while preventing interference with any protruding portion of the object. In addition, since switching is performed by only rotating operation with only the Θ axis and the distance from the center of rotation to the eye E is constant, the positions of the optometric unit 110 in the X and Y directions are reproduced and an operating distance in the Z direction required for eye pressure measurement can be automatically obtained. This makes it unnecessary to perform rough alignment after switching operation, and can further shorten the optometry time. After switching operation, the apparatus starts fine alignment for the right eye ER of the object. Upon completing fine alignment, the apparatus measures the eye pressure of the right eye ER a predetermined number of times (FIG. 9C). Upon completing eye pressure measurement of the right eye ER, the apparatus moves the optometric unit 110 in the X and Z directions by necessary amounts and measures the eye pressure of the left eye EL a predetermined number of times (FIG. 9D).

(Third Embodiment)

An ophthalmic apparatus according to the third embodiment will be described with reference to FIG. 10. This embodiment will exemplify an arrangement configured to switch the inspection modes by rotating a rotating unit 251 (switching unit) of an optometric unit 110 instead of rotating the overall optometric unit 110. The rotating unit 251 (switching unit) includes optical elements (for example, a dichroic mirror 252 and the like) commonly used by first and second optometric units, and can switch between the first and second optometric units by changing the direction of a switching optical element unit relative to an eye to be examined. The optometric unit 110 is fixed on a frame 107 which can move in a direction (Z direction) to approach or recede from the eye to be examined. The rotating unit 251 is coupled to the output shaft of a Θ-axis driving motor 116 (driving unit) fixed on the optometric unit 110, and can rotationally move around a rotation axis (Θ-axis) relative to the optometric unit 110. In the arrangement shown in FIG. 10, the optometric unit 110 is fixed on the frame 107. However, the scope of the present invention is not limited to this example. For example, as shown in FIG. 1, the optometric unit 110 can be configured to be rotatable relative to the frame 107.

Figure 10:
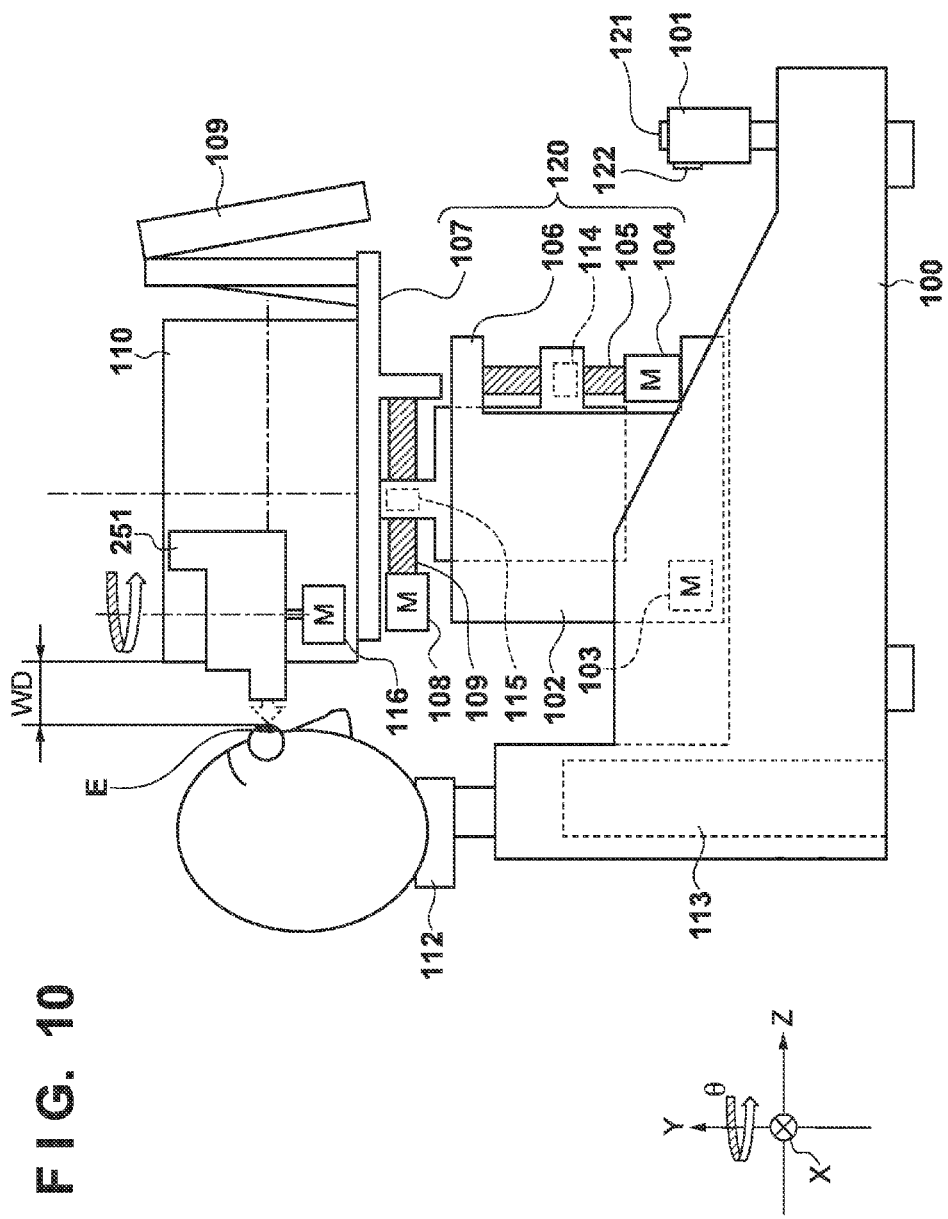
FIG. 10 is a view showing the schematic arrangement of an ophthalmic apparatus according to the third embodiment.
Figure 11A:
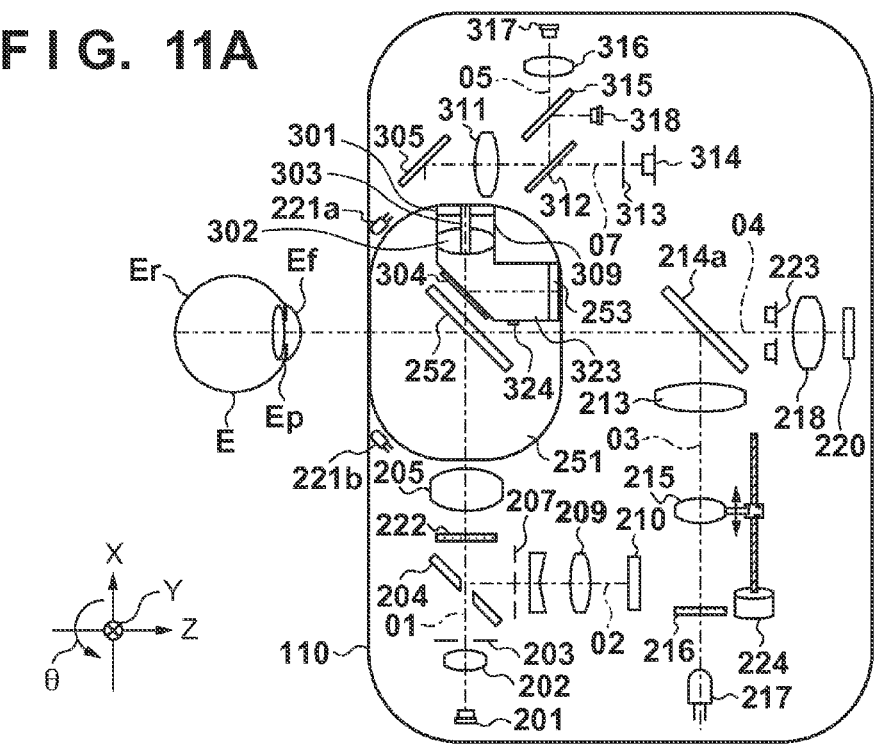
FIGS. 11A and 11B are views showing the arrangement of the optical system of the optometric unit of the ophthalmic apparatus according to the third embodiment.
Figure 11B:
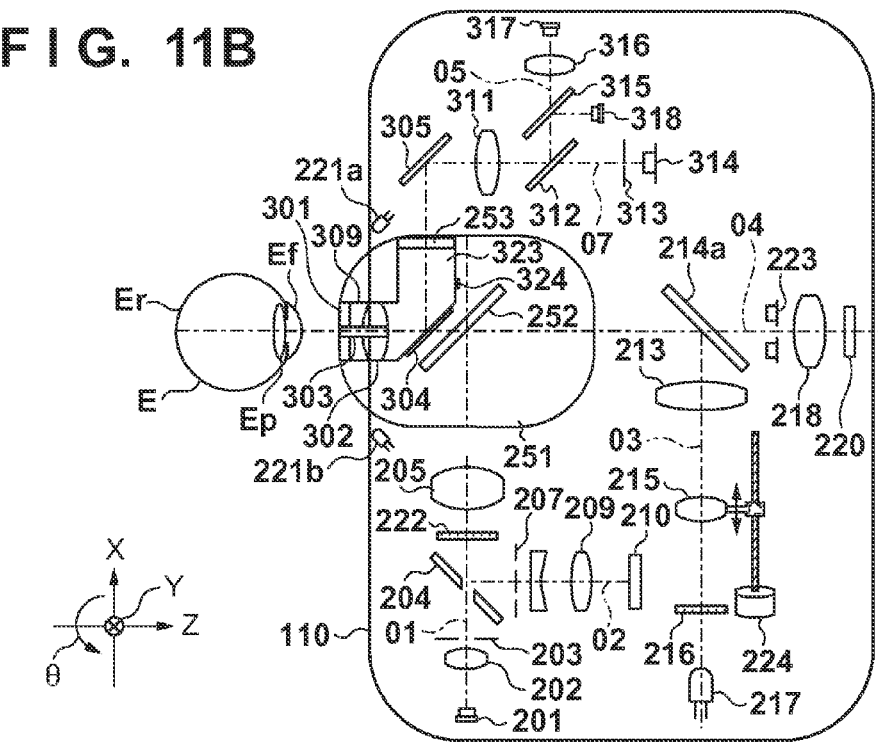

FIGS. 11A and 11B are views showing the arrangement of an optical system in the optometric unit 110 shown in FIG. 10.

(First Optical system)

FIG. 11A is a view showing the arrangement of the optical system in the optometric unit 110 at the time of measurement of an ocular refractive power. A projection lens 202, a stop 203 almost conjugate to a pupil Ep of an eye E to be examined, a perforated mirror 204, and a lens 205 are arranged on an optical path 01 extending from an ocular refractive power measurement light source 201 for emitting light with a wavelength of 880 nm to the eye E. In addition, a dichroic mirror 252 is disposed next to the above components on the optical path. The dichroic mirror 252 partly reflects infrared and visible light with wavelengths less than 880 nm and totally reflects a light beam with wavelengths of 880 nm or more from the eye E side. The dichroic mirror 252 is disposed in a rotating unit 251. A stop 207 which includes an annular slit and is almost conjugate to the pupil Ep, a light beam spectral prism 208, a lens 209, an image sensor 210 are sequentially disposed on an optical path 02 in the reflecting direction of the perforated mirror 204.

The above optical system is used for ocular refractive power measurement, in which the stop 203 restricts the light beam emitted from the ocular refractive power measurement light source 201. The projection lens 202 performs primary image formation in front of the lens 205. The resultant light beam is transmitted through the lens 205, reflected by the dichroic mirror 252, and projected onto the pupil center of the eye E. The reflected light of the projected light beam passes through the pupil center and enters the lens 205 again. The incident light beam is transmitted through the lens 205 and then reflected by the periphery of the perforated mirror 204.

The stop 207 almost conjugate to the pupil Ep of the eye to be examined and the light beam spectral prism 208 pupil-split the reflected light beam. The resultant light beam is projected as a ring image on the light-receiving surface of the image sensor 210. On the other hand, a visual fixation target projection optical system and an alignment light-receiving optical system used for both anterior ocular segment observation and alignment detection are arranged in the transmission direction of the dichroic mirror 206.

A dichroic mirror 214a, a lens 213, a lens 215, a visual fixation target 216, and a visual fixation target illumination light source 217 are sequentially arranged on an optical path 03 of the visual fixation target projection optical system.

At the time of visual fixation guidance, the projection light beam emitted from the visual fixation target illumination light source 217 in an ON state illuminates the visual fixation target 216 from the back side. The light beam is then projected onto a fundus Er of the eye E through the lens 215, the lens 213, and the dichroic mirror 214a.

Note that a visual fixation target guide motor 224 can move the lens 215 in the optical axis direction so as to implement a fogging state by performing visual fixation guidance for the eye E.

An alignment prism stop 223 which is inserted and removed by an alignment prism stop insertion/removal solenoid 411, an imaging lens 218, and an image sensor 220 are sequentially arranged on an optical path 04 in the transmission direction of the dichroic mirror 214a. Inserting and removing the alignment prism stop 223 can perform alignment when the alignment prism stop 223 is located on the optical path 04 and can perform anterior ocular segment observation or transillumination observation when the alignment prism stop 223 is retracted from the optical path.

(Second Optical System)

FIG. 11B is a view showing the arrangement of the optical system in the optometric unit 110 at the time of measurement of an eye pressure. On a light-receiving optical path and alignment detection optical path 04 of an observation optical system for the eye E, a nozzle 303 is disposed on the central axis of a plane parallel glass plate 301 and objective lens 302. An air chamber 323, an observation window 304, the dichroic mirror 252, the dichroic mirror 214a, the prism stop 223, the imaging lens 218, and the image sensor 220 are sequentially arranged behind the objective lens 302. An objective lens barrel 309 supports the plane parallel glass plate 301 and the objective lens 302. Light sources 221a and 221b functioning as extraocular illumination light sources for illuminating the eye E are arranged outside the objective lens barrel 309.

A plane parallel glass plate 253 is disposed on an optical path 07 of a deformation detection light-receiving optical system when a cornea Ef deforms in the visual axis direction a relay lens 311, a half mirror 312, an aperture 313, and a light-receiving element 314 are arranged in the reflecting direction of a dichroic mirror 305. Note that the aperture 313 is disposed at a position at which it is conjugate to a cornea reflected image of an eye pressure measurement light source 317 (to be described later) at the time of predetermined deformation. The relay lens 311 is designed to form a cornea reflected image almost equal in size to the aperture 313 when a cornea Ec deforms into a predetermined shape.

A half mirror 315 and a projection lens 316 are arranged, in the incident direction of the half mirror 312, on an optical path 05 of a measurement light source projection optical system for measuring the deformation of the cornea Ef. In addition, the eye pressure measurement light source 317 formed from a near-infrared LED used for both measurement and alignment for the eye E is disposed on the above optical path. Furthermore, a visual fixation light source 318 formed from an LED for visual fixation by an object is disposed in the incident direction of the half mirror 315.

Figure 12:
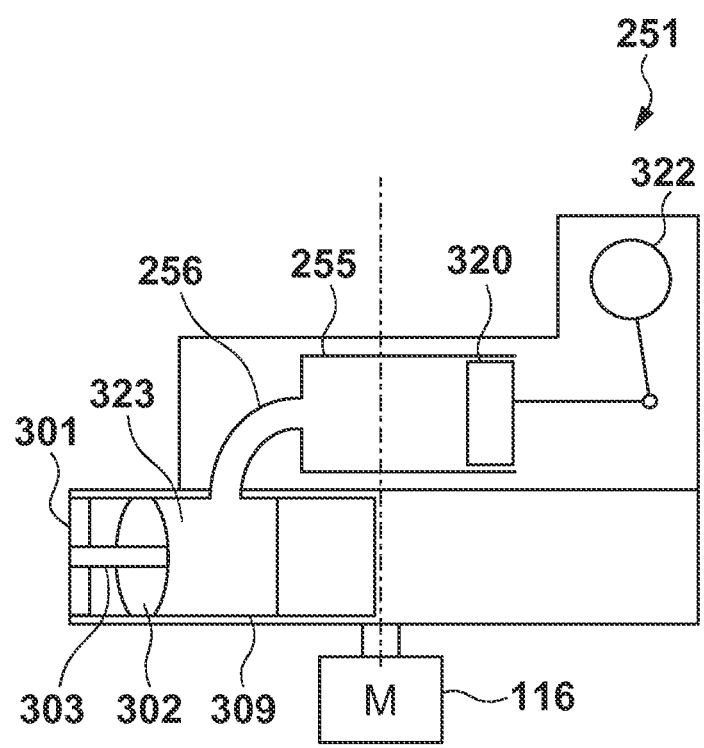
FIG. 12 is a side view of a rotating unit.

FIG. 12 is a side view of the rotating unit 251. The interior of an air chamber 323 communicates with a cylinder 255 in the upper portion of the rotating unit 251 through a pipe 256. A piston 320 is fitted in the cylinder 255. A solenoid 322 drives the piston 320. Note that a pressure sensor 324 (FIGS. 11A and 11B) for monitoring an internal pressure is disposed in the air chamber 323.

FIGS. 13A and 13B are plan views showing the relative positional relationship between the rotating unit 251 on the optometric unit 110 and an eye to be examined. FIG. 13A shows the positional relationship between the rotating unit 251 and the eye to be examined at the time of measurement of an ocular refractive power. FIG. 13B shows the positional relationship between the rotating unit 251 and the eye to be examined at the time of measurement of an eye pressure. The rotating unit 251 rotationally moves around a center of rotation 350 (Θ direction) relative to the optometric unit 110. Let WD1 be an operating distance at the time of measurement of an ocular refractive power, that is, the distance from a cornea vertex Ef of the eye E to the first optical system output-side end portion of the optometric unit 251, and A be the distance from the center of rotation 350 to the first optical system output-side end portion of the optometric unit 251. In addition, let WD2 be an operating distance at the time of measurement of an eye pressure by a second optical system 300, that is, the distance from the cornea vertex Ef of the eye E to the second optical system output-side end portion of the optometric unit 251, and B be the distance from the center of rotation 350 to the second optical system output-side end portion of the optometric unit 251. In this case, the optometric unit 251 and the center of rotation 350 are configured to make the difference (WD1−WD2) between the operating distances equal to the difference (B−A) between the distances from the center of rotation to the output-side end portions, that is, satisfy WD1+A=WD2+B.

The above arrangement can obtain the same effects as those of the first embodiment and allows the common use of the prism stop, imaging lens, image sensor, and extraocular illumination light source of the observation optical system. This makes it possible to reduce the size and cost of the apparatus.

The ophthalmic apparatus according to the embodiment of the present invention is a composite type ophthalmic apparatus. When switching one type of inspection by the optometric unit 110 to a different type of inspection, the driving mechanism in the Θ-axis direction (optometric unit moving unit) moves the optometric unit 110 in a rotational direction relative to a base 100 (apparatus fixing unit). For the sake of simplicity, according to the above embodiments, the functions to be combined are limited to the ocular refractive power function and the eye pressure function. However, the present invention can be applied to an ophthalmic apparatus which additionally includes other optometry functions such as a cornea curvature radius measurement function and a cornea thickness measurement function. In addition, optometry functions to be added are not limited to measurement functions. The present invention can be applied to general ophthalmic apparatuses which perform inspections concerning the eye to be examined, for example, a fundus camera and an OCT apparatus.

Although the rotating mechanism for the optometric unit 110 in this embodiment is a mechanism using pulleys and belts, the scope of the present invention is not limited to this arrangement. For example, the output shaft of a motor may be directly coupled to the optometric unit and rotate. Alternatively, a rotating mechanism may be formed by using other mechanisms such a chain driving mechanism.

The order of inspections is not limited to ocular refractive power measurement→eye pressure measurement and right eye optometry→left eye optometry. The present invention can be applied to an arbitrary order of inspections. The driving mode to be used is not limited to full automatic driving. The present invention can be applied to the manual driving mode, semi-automatic driving mode, and the like.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-104885, filed May 1, 2012, which is hereby incorporated by reference herein in its entirety.

What is claimed is:

1. An ophthalmic apparatus which is configured to inspect a plurality of eye characteristics of an eye to be examined, the apparatus comprising:

an optometric unit configured to include (a) a first optometric portion including a first optical system for inspecting a first eye characteristic of the eye, (b) a second optometric portion including a second optical system for inspecting a second eye characteristic different from the first eye characteristic, and (c) a switching unit which includes an optical element commonly used by said first optometric portion and said second optometric portion and which is configured to switch an optical path to one of said first optometric portion and said second optometric portion by changing a direction of said optical element relative to the eye.

2. The apparatus according to claim 1, further comprising a driving unit configured to rotate said switching unit to change a direction of said optical element relative to the eye.

3. The apparatus according to claim 2, wherein a sum (WD1 +A) of an operating distance (WD1) of said first optometric portion constituted by said switching unit and said first optical system and a distance (A) from a center of rotation of said driving unit to an end portion of said first optometric portion is equal to a sum (WD2 +B) of an operating distance (WD2) of said second optometric portion constituted by said switching unit and said second optical system and a distance (B) from the center of rotation of said driving unit to an end portion of said second optometric portion.

4. The apparatus according to claim 2, further comprising an optometric unit moving unit configured to position said optometric unit at a position to inspect the eye,
wherein said optometric unit inspects the eye upon completion of positioning by said optometric unit moving unit,
wherein said driving unit switches from inspection by said first optometric portion to inspection by said second optometric portion by rotating said switching unit at the position at which positioning is performed by said optometric unit moving unit, upon completion of inspection by said first optometric portion of said optometric unit, and
wherein said driving unit switches from inspection by said second optometric portion to inspection by said first optometric portion by rotating said switching unit at the position at which positioning is performed by said optometric unit moving unit, upon completion of inspection by said second optometric portion of said optometric unit.

5. The apparatus according to claim 2, further comprising a control unit configured to control said driving unit so as to rotate said switching unit in accordance with an instruction for switching an inspection by said first optometric portion and an inspection by said second optometric portion.

6. The apparatus according to claim 2, further comprising a control unit configured to control said driving unit so as (a) to inspect one eye of left and right eyes of an object by using said first optometric portion, (b) to inspect the other eye of the left and right eyes by using said first optometric portion after said optometric unit completes movement to a position for inspecting the other eye, and (c) to inspect the other eye by using said second optometric portion after said optometric unit completes inspection for the other eye.

7. The apparatus according to claim 1, further comprising a display unit configured to display an image of the eye inspected by said optometric unit.

8. The apparatus according to claim 1, wherein said first optometric portion comprises an optometric portion including an optical system configured to inspect an ocular refractive power of the eye, and
wherein said second optometric portion comprises an optometric portion including an optical system configured to inspect an eye pressure of the eye.

9. The apparatus according to claim 1, wherein said optical element includes a dichroic mirror configured to branch an optical path of the first optical system and an optical path of the second optical system.

10. The apparatus according to claim 1, further comprising an image sensing unit configured to be disposed on a common optical path commonly used by a part of an optical path of said first optometric portion and a part of an optical path of said second optometric portion, and to capture an image of the eye to be examined,
wherein said optical element is disposed on the common optical path.

11. The apparatus according to claim 10, wherein an objective optical element of said first optometric portion and an objective optical element of said second optometric portion are disposed on optical paths which differ from the common optical path, and
wherein each of the objective optical element of said first optometric portion and the objective optical element of said second optometric portion is switched by switching, by said switching unit, of the optical paths.

12. An ophthalmic apparatus which is configured to inspect a plurality of eye characteristics of an eye to be examined, the apparatus comprising:
an optometric unit configured to include (a) a first optometric portion including a first optical system for inspecting a first eye characteristic of the eye, and (b) a second optometric portion including a second optical system for inspecting a second eye characteristic different from the first eye characteristic; and
a changing unit configured to change a direction of said optometric unit relative to the eye.

13. The apparatus according to claim 12, further comprising an optometric unit moving unit configured to position said optometric unit at a position to inspect the eye,
wherein said optometric unit inspects the eye upon completion of positioning by said optometric unit moving unit, and
wherein said changing unit changes a direction of said optometric unit at the position at which positioning is performed by said optometric unit moving unit, upon completion of inspection by one of said first optometric portion and the said second optometric portion.

14. The apparatus according to claim 12, further comprising a driving unit configured to rotate said changing unit to change the direction of said optometric unit relative to the eye.

15. The apparatus according to claim 14, further comprising a control unit configured to control said driving unit so as to rotate said changing unit in accordance with an instruction for switching an inspection by said first optometric portion and an inspection by said second optometric portion.

16. The apparatus according to claim 14, further comprising a control unit configured to control said driving unit so as to rotate said changing unit from an ear side of an object to a nose side of the object in accordance with an instruction for switching an inspection by said first optometric portion and an inspection by said second optometric portion.

17. The apparatus according to claim 14, further comprising a control unit configured to control said driving unit so as (a) to inspect one eye of left and right eyes of an object by using said first optometric portion, (b) to inspect the other eye of the left and right eyes by using said first optometric portion after said optometric unit completes movement to a position for inspecting the other eye, and (c) to inspect the other eye by using said second optometric portion after said optometric unit completes inspection for the other eye.

18. The apparatus according to claim 12, further comprising:
- a member configured to fix said optometric unit to an apparatus fixing unit;
- a driving unit configured to drive said member; and
- a control unit configured to control said driving unit so as to fix said optometric unit to said apparatus fixing unit after the direction of said optometric unit relative to the eye is changed.

19. The apparatus according to claim 18, wherein said control unit controls said driving unit so as to insert said member into a groove portion of said apparatus fixing unit.

* * * * *